(12) United States Patent
Shapiro et al.

(10) Patent No.: US 6,609,071 B2
(45) Date of Patent: Aug. 19, 2003

(54) SYSTEM FOR MONITORING AND CONTROLLING PRESSURE AND CONCENTRATION VALUES IN A FLUID CONDUIT

(75) Inventors: Philip Shapiro, Frederick, MD (US); John Davis-Reinhold, Frederick, MD (US); Julian Warhurst, Ashland, MA (US); Charles Daniel Hayes, Glen Burnie, MD (US)

(73) Assignee: Project CD, Frederick, MD (US)

( * ) Notice: Subject to any disclaimer, the term of this patent is extended or adjusted under 35 U.S.C. 154(b) by 481 days.

(21) Appl. No.: 09/729,703

(22) Filed: Dec. 6, 2000

(65) Prior Publication Data

US 2002/0069023 A1 Jun. 6, 2002

(51) Int. Cl.⁷ .............................................. G06F 19/00
(52) U.S. Cl. ............................. 702/50; 702/51; 604/30
(58) Field of Search ........................ 604/30, 31, 508, 604/65, 67, 151; 702/50, 53

(56) References Cited

U.S. PATENT DOCUMENTS

| | | | |
|---|---|---|---|
| 4,529,397 A | * | 7/1985 | Hennemuth et al. ....... 604/6.09 |
| 5,006,997 A | * | 4/1991 | Reich .......................... 600/561 |
| 5,477,468 A | | 12/1995 | Shapiro et al. ............. 364/499 |
| 6,468,241 B1 | * | 10/2002 | Gelfand et al. ............ 604/6.09 |

* cited by examiner

Primary Examiner—John Barlow
Assistant Examiner—Stephen J. Cherry
(74) Attorney, Agent, or Firm—Hunton & Williams

(57) ABSTRACT

A system for monitoring and regulating pressure and concentration in a moving fluid stream inside of a conduit is provided. The fluid stream includes a first fluid. The system comprises an infusion assembly that includes a catheter having a series of holes distributed around an exterior surface and a pumping system for introducing a second fluid into said catheter to create a solution mixture. A data collection system is provided for collecting data indicative of pressure and conductivity values. Data from the data collection system is forwarded to a data processing and control apparatus. The data processing and control apparatus comprises conversion means for converting the measured conductivity into a concentration value and control means for controlling operation of the infusion assembly based on a comparison of selected values with data received from the data collection system. A user control and analysis system allows user interaction. The system allows complete automatic control over the fluid distribution within a fluid conduit in response to measured values.

31 Claims, 16 Drawing Sheets

SYSTEM FOR MONITORING AND CONTROLLING PRESSURE AND CONCENTRATION VALUES IN A FLUID CONDUIT

FIELD OF THE INVENTION

The present invention relates to a system for monitoring and regulating fluid concentration and fluid pressure within a fluid conduit. Specifically, the system monitors and controls a concentration and a pressure value in an arterial or a venous line during continuous fluid flow.

BACKGROUND OF THE INVENTION

Traditionally, it has been difficult to obtain accurate data about fluid concentrations within a fluid stream without using an invasive technique. U.S. Pat. No. 5,477,468, hereby incorporated by reference, discloses a concentration analyzer that achieves instantaneous measurement of fluid concentration in a moving fluid stream. However, the system disclosed in the prior patent did not provide any mechanism for measuring or controlling pressure within a fluid conduit.

There is also a need for a system for measuring and controlling the delivery and dispersion of an anticoagulant agent, a radio-opaque contrast agent, and various other chemical agents entering an artery or a vein.

There is also a need for a system to effectively monitor and regulate pressure variations within a fluid conduit.

SUMMARY OF THE INVENTION

It is therefore an object of the invention to provide a system that allows complete control over the distribution of a fluid entering an artery or a vein.

It is an additional object of the present invention to provide a pressure measurement system that effectively monitors and regulates pressure variations within a fluid conduit.

It is an additional object of the invention to provide a system that effectively monitors pressure variations and concentration variations within a fluid conduit and that automatically controls fluid flow in response to a variation.

Additional objects and advantages of the invention will be set forth in part in the description which follows, and in part will be obvious from the description, or may be learned by practice of the invention. The objects and advantages of the invention may be realized and obtained by means of the instrumentalities and combinations particularly pointed out in the appended claims.

To achieve the objects and in accordance with the purposes of the invention as embodied and broadly described herein, a system is provided for monitoring and regulating pressure in a moving fluid stream inside of a conduit. The system comprises an infusion assembly including a catheter having a series of holes distributed around an exterior surface. The infusion assembly further includes injection means for introducing a fluid into the catheter and a pump for delivering fluid to the injection means. The invention further comprises a data collection system including a first pressure transducer attached to a pressure chamber of the pump and a second pressure transducer attached to the end of the catheter for measuring the pressure in a pressure chamber line of the catheter. A data processing and control system is provided for processing data collected from the second pressure transducer attached to the end of the catheter and for controlling operations of the infusion assembly based on a comparison of a plurality of selected values and the data received from the data collection system. A user control and analysis system allows user interaction.

In an additional aspect of the invention, a system is provided for monitoring and regulating pressure and concentration in a moving fluid stream inside of a conduit, wherein the fluid stream includes a first fluid. The system comprises an infusion assembly including a catheter having a series of holes distributed around an exterior surface and injection means for introducing a second fluid into the catheter to create a solution mixture, and a pump for delivering the second fluid to the injection means. A data collection system is provided that includes a first pressure transducer attached at a first end of the catheter for measuring the pressure in a pressure chamber line of the catheter, a second pressure transducer attached at a second end of the catheter, and a sensor means within the conduit for measuring a conductivity of the first and second solution mixture. A data processing and control apparatus is provided that includes conversion means for converting the measured conductivity into a concentration value, and control means for controlling operation of the infusion assembly based on a comparison of a plurality of selected values with data received from the data collection system. A user control and analysis system allows user interaction.

The accompanying drawings, which are incorporated in and constitute a part of this specification, illustrate an embodiment of the invention and, together with the description, serve to explain the principles of the invention.

DETAILED DESCRIPTION OF THE PREFERRED EMBODIMENTS

Figure 1:
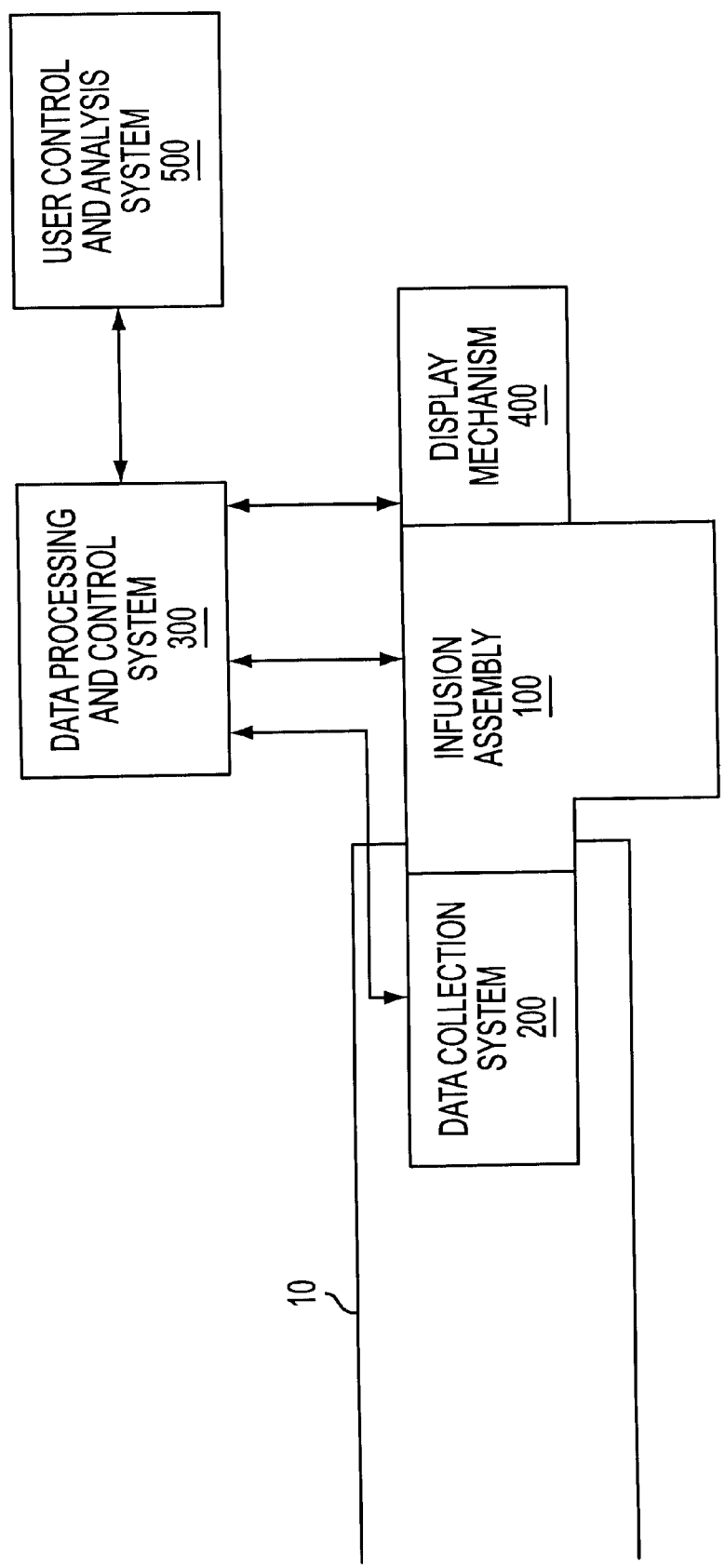
FIG. 1 is a block diagram illustrating the main components of the system of the invention.

Reference will now be made in detail to the present preferred embodiments of the invention, examples of which are illustrated in the accompanying drawings in which like reference numerals refer to corresponding elements.

FIG. 1 is a block diagram illustrating the major components of an embodiment of a system for monitoring and regulating pressure in a moving fluid stream inside of a conduit in accordance with the invention, fluid monitoring and control system 1. An infusion assembly 100 provides fluid flow through a conduit 10. The system 1 of the invention is particularly suited for use in a conduit 10 such as a human vein or an artery. A data collection system 200 collects data related to the fluid flow through the conduit 10. From the data collection system 200, one or more data signals are transmitted to a data processing and control system 300, which processes data for display on a display mechanism 400 and further controls the infusion assembly 100 with the processed data. A user control and analysis system 500 allows user input and communicates with the data processing and control system 300 to receive processed data and convey selected values. Each of the aforementioned subsystems is explained in further detail below.

A. Infusion Assembly 100

Figure 2A:
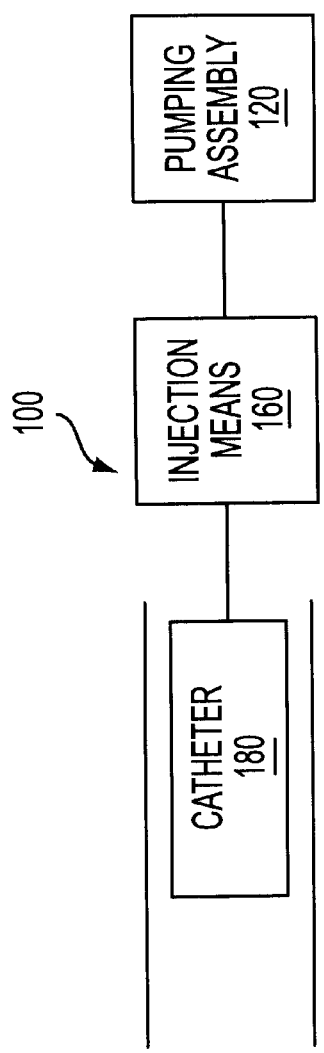
FIG. 2a is a block diagram showing the components of the infusion assembly.

FIG. 2a illustrates the components of the infusion assembly 100. The infusion assembly 100 includes a pumping assembly 120, an injection means 160, and a catheter 180. These portions of the infusion assembly 100 will be described in greater detail below.

1. Catheter 180

Figure 2B:
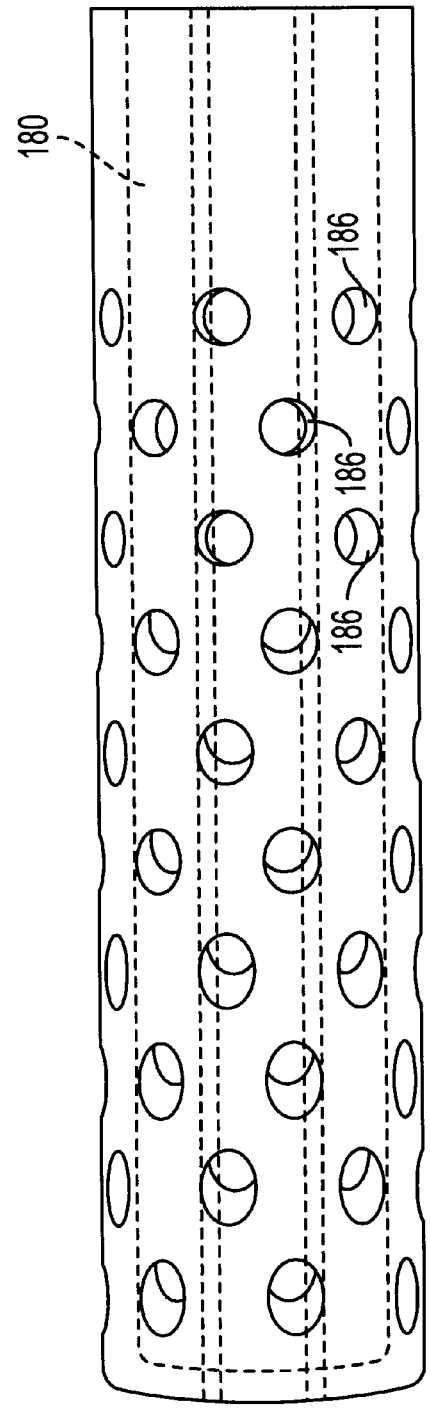
FIG. 2b is a side view showing an embodiment of the catheter of the infusion assembly.
Figure 8A:
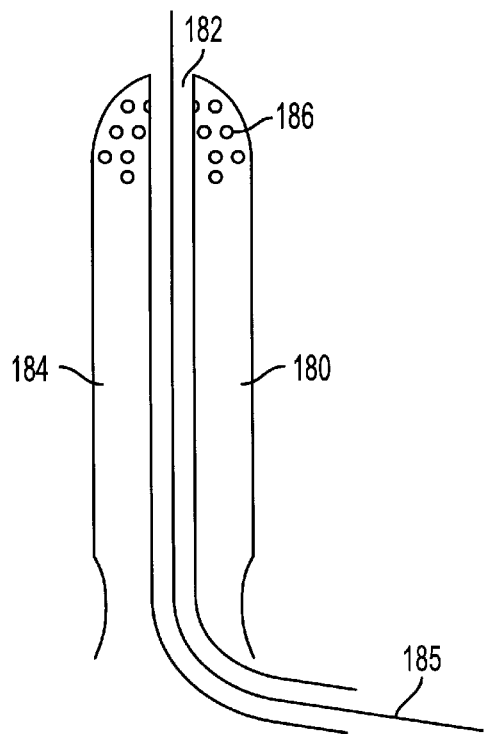
FIGS. 8a and 8b illustrate insertion of the catheter.
Figure 8B:
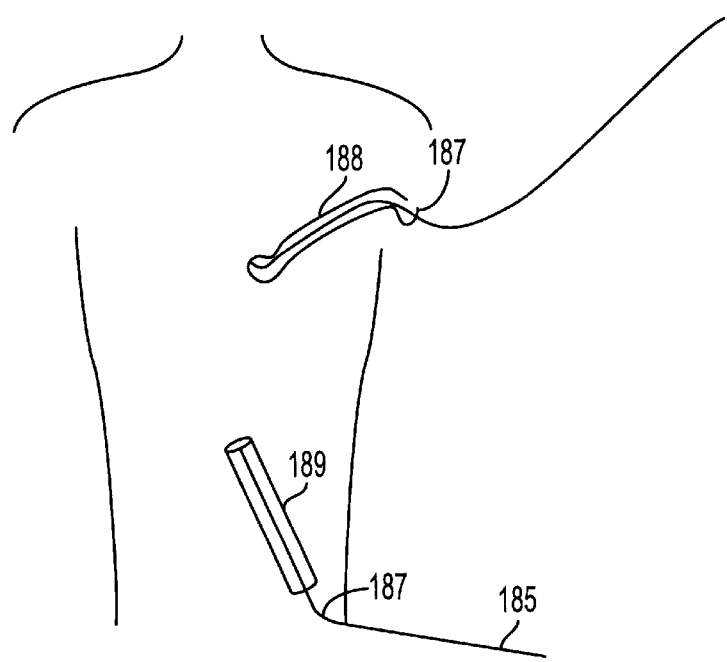

FIG. 2b illustrates catheter 180, which preferably is inserted into the conduit 10, which may be a vein or an artery of a human patient, in a conventional fashion using a guide wire 185 as shown in FIGS. 8a and 8b. The guide wire 185 is subsequently removed after insertion of the catheter 180. The catheter 180 is adapted for mounting one or more data collection components to be described in more detail below.

FIGS. 8a and 8b further illustrate the components of the catheter 180 and a technique for its insertion. A commercially available guide wire 185 made from a thin, highly flexible alloy is used to guide insertion of the catheter 180 into the conduit 10. The guide wire 185 comes in a plurality of diameters to accommodate catheters of varying sizes.

Current practice is to introduce an angiographic needle for injection at a point of introduction 187 to an artery as shown in FIG. 8b. The angiographic needle has a steel rod, called a stylette (not shown), through its center. The angiographic needle is introduced through the skin at the point of introduction 187 into the artery with the stylette in place. The stylette is then pulled out and the guide wire 185 is introduced through the angiographic needle. The angiographic needle is then removed by passing it over the guide wire 185. The catheter 180 is then passed over the guide wire 185 via a pressure space 182 of the catheter 180 and the guide wire 185 is then pulled out. A piezo-resistive transducer 214 (described in detail below) is then connected to the pressure space 182 and pumping can begin through a pumping space 184 of the catheter 180.

The guide wire 185 is necessary for insertion because, without it, the catheter 180 may become off-center and cause damage to the arterial wall. The guide wire 185 is very flexible and will not cause damage to the arterial wall.

Measuring devices such as transducers cannot be placed on the side of the catheter 180, because they also may cause damage to the arterial wall.

FIG. 8b illustrates a need for two different types of guide wires 185. Artery 187 is a curved brachial artery which requires a guide wire 185 with an angled tip. Artery 189 is a straight femoral artery which requires a guide wire 185 with straight tip. In either case, the guide wire 185 has a proximal end that is more flexible than a distal end.

The catheter 180 should include a plurality of holes 186. Preferably, a total surface area of all of the holes 186 is roughly equivalent to a total cross-sectional area of the conduit 10 in order to obtain an effective flow. The holes 186 should point in all directions in order to ensure an equal distribution of fluid throughout the conduit 10. Optimally, the catheter 180 is disposed in operation centrally within the conduit 10. In a preferred embodiment, the catheter 180 should include about seventy holes 186. Because conduit 10 sizes will vary, catheters 180 providing different aperture sizes should be provided. A diaphragm (not shown) including a puncturable latex or rubber inserted in a brass fitting is provided in an embodiment of the invention to facilitate insertion of the catheter 180 into the conduit 10.

2. Injection Means 160

Figure 2C:
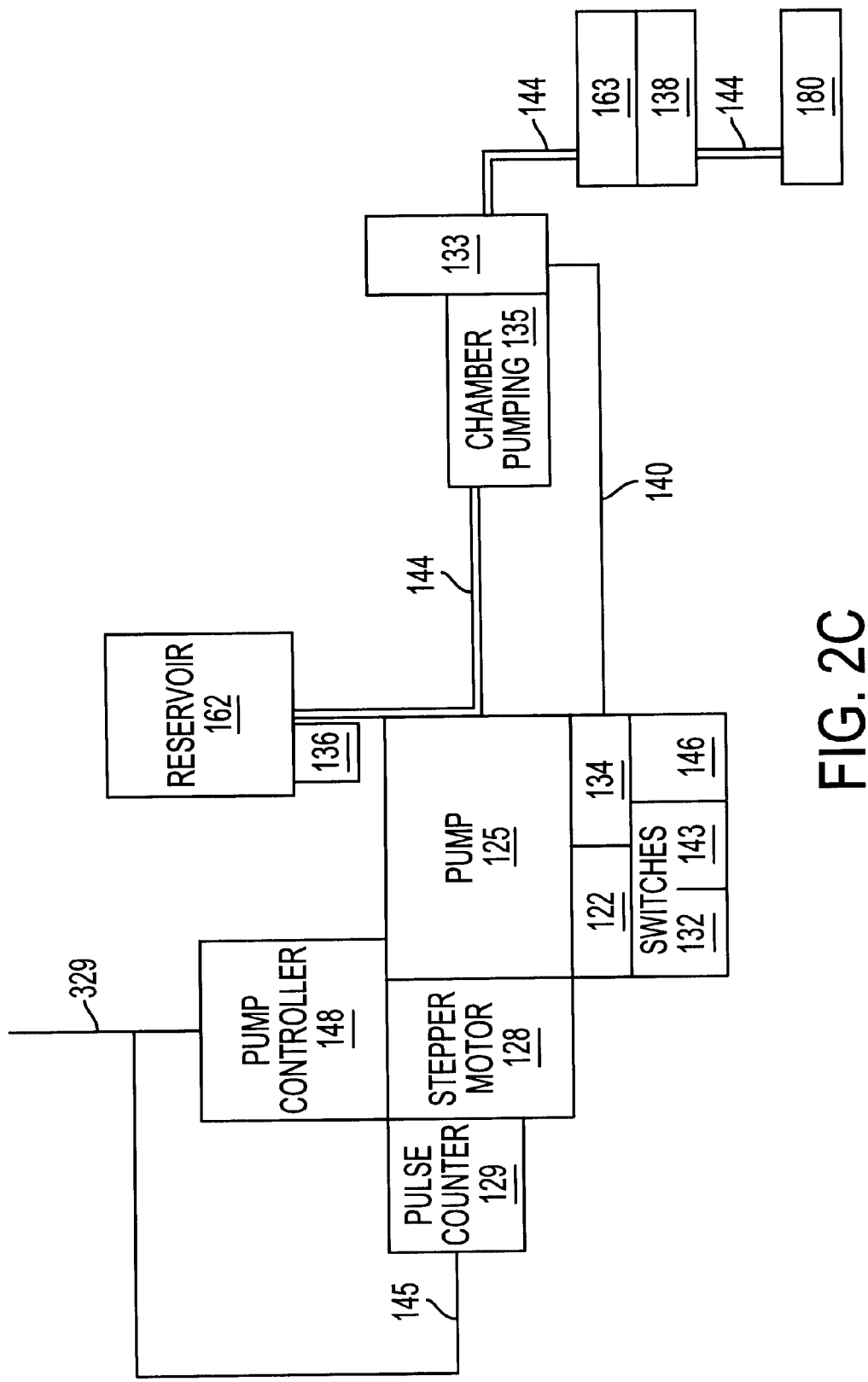
FIG. 2c is a diagram showing the pumping components and injection means of the infusion assembly.

FIG. 2c illustrates a plurality of components of the injection means 160. A syringe 163 is provided for injecting fluid into the catheter 180. A reservoir 162, filled with the fluid to be pumped, is operatively connected with the syringe 163. Reservoir 162 enables refilling of syringe 163 when prompted by the data processing and control system 300.

3. Pumping Components

Also as shown in FIG. 2c, a pump 125 is provided for pumping fluid from the above-described reservoir 162 to syringe 163 for injection into catheter 180. Pump 125 is preferably a pulsatile pump with a capability of pumping 25,000 pulses per second and is provided with varying pulse rates and a fixed pulse volume. The catheter 180 is inserted into a circulatory system emulates a human circulatory system by providing multiple fluid pathways, adjustable compliance and adjustable resistance for purposes of experimentation.

Pump 125 is powered by a stepper motor 128. A plurality of drive components 122 for pump 125 preferably include a linear drive shaft and a belt to deliver the stepper motor 128 output to a syringe pumping chamber 135. The syringe pumping chamber 135 preferably handles pumping pressures of up to 500 pounds per square inch (PSI). The pumping chamber 135 is preferably constructed of a thick heavy duty transparent plastic. A pressure switch 132 is provided for setting the desired pumping pressure in order to enable pumping at a constant pressure.

A wire 145 delivers a plurality of electronic signals to a stepper motor pulse counter 129. The electronic signals delivered are those which originated by tapping into the line from the pressure monitor 320 (further described below) to the stepper motor controller 148. The stepper motor pulse counter 129 counts and displays a cumulative number of pulses of the stepper motor 128.

Stepper motor 128 maintains a constant pressure in the syringe 163 as set by the pressure switch 132. A pumping electronic switch 143 provides an electronic signal to indicate when the syringe 163 is full. A refill electronic switch 146 provides an electronic signal indicating that the syringe 163 is empty. In a preferred embodiment of the invention, both the pumping electronic switch 143 and the refill electronic switch 146 remain open until the syringe 163 is either empty or full, in which case, the appropriate switch closes. A suitable switch for use for the pumping electronic switch 143 and the refill electronic switch 146 includes a Cherry E61 subminiature switch rated at 5 amps, 125/250 volts AC.

A crack valve 136 is provided that permits fluid to flow only in one direction from the reservoir 162 to the syringe 163 when the syringe 163 is refilling. A bleeder valve 138 facilitates removal of all of the air and bubbles from the syringe 163 before pumping is commenced.

A solenoid valve 133, which preferably has less than a 4 millisecond delay, controls pumping from the syringe 163 into the catheter 180. Solenoid valve 133 is connected with a solenoid valve circuit board 134 via a wire 140. In operation, fluid moves directly from the pump 125 to the solenoid valve 133, into the catheter 180.

A low compliance connecting tube 144 is provided to deliver flow through the pump 125, the solenoid valve 133, and subsequently into the catheter 180.

If the solenoid valve 133 is continuously open, then the pump 125 operates continuously. The pump 125 is controlled directly from a pressure monitoring system 320 that is described below.

Figure 2D:
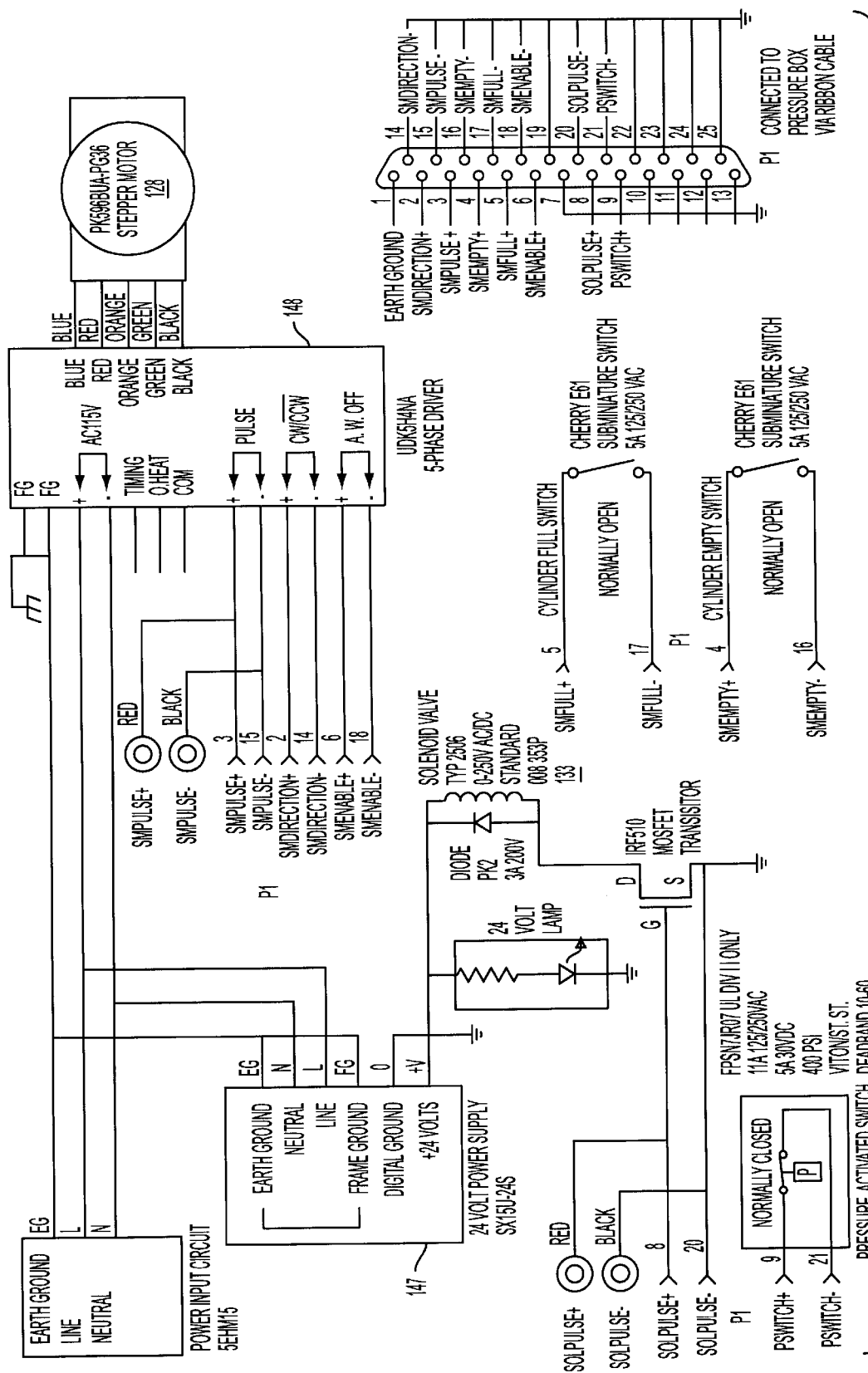
FIG. 2d is a circuit diagram showing connections within the infusion assembly.

FIG. 2d is a circuit diagram showing the preferred connections between solenoid valve 133 and stepper motor 128. A plurality of pulses 301 are sent from the data processing and control system 300 to control the solenoid valve 133. Solenoid valve 133 is selectively operates by a power supply 147, which transmits signals to a stepper motor controller 148, which is preferably a 5-phase driver, to operate the stepper motor 128.

B. Data Collection System 200

1. Pressure Data Collection Subsystem 210

Figure 4:
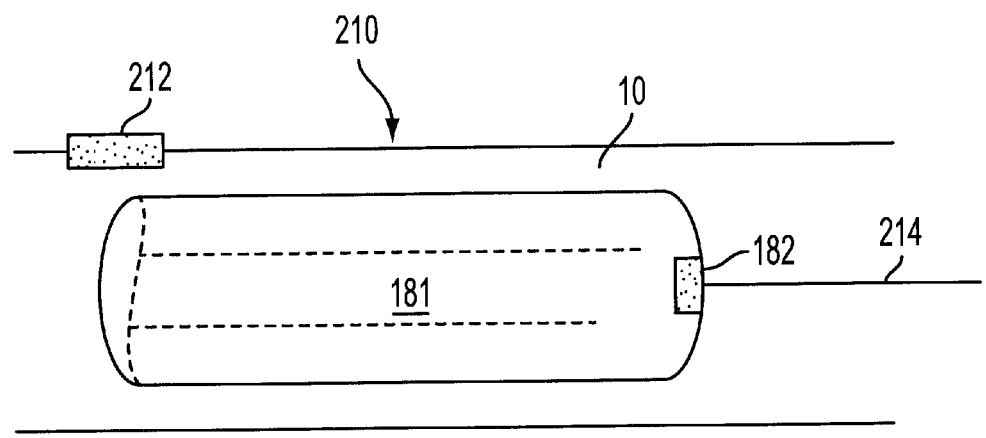
FIG. 4 illustrates the pressure data collection apparatus for the data collection system.

As shown in FIG. 4, the data collection system 200 preferably includes a pressure data collection subsystem 210, that includes two transducers in an experimental mode for measuring pressure. Each of the two pressure transducers is attached to an end of the catheter 180. A first signal is received from a Harvard pressure transducer 212 at a first distal end of the catheter 180 and a second signal is received from a piezo-resistive transducer 214 at an opposite proximal end of the catheter 180. The piezo-resistive transducer 214 preferably includes a steel diaphragm and has a resonant frequency of approximately 50 khz. Harvard pressure transducer 212 is a non piezo-resistive transducer placed into the wall of the plastic tubing adjacent to the tip of the catheter 180. The Harvard pressure transducer 212 is used during experimentation for gathering data. Once the necessary experimental data is gathered, the Harvard pressure transducer 212 is removed for actual use of the catheter 180 during treatment.

Piezo-resistive transducer 214 measures the pressure in a pressure chamber line 181 of the catheter 180. The pressure chamber line 181 of catheter 180 delivers the pressure wave from the tip of the catheter 180 to the piezo-resistive transducer 214. Accordingly, pressure measurements are taken at both ends of the catheter 180 and the delay between the generated signals is taken into account. A wire 182 delivers the electronic signal from the piezo-resistive transducer 214 to a pressure monitoring subsystem 320 of the data processing and control system 300.

2. Conductivity Data Collection Subsystem 230

Figure 5A:
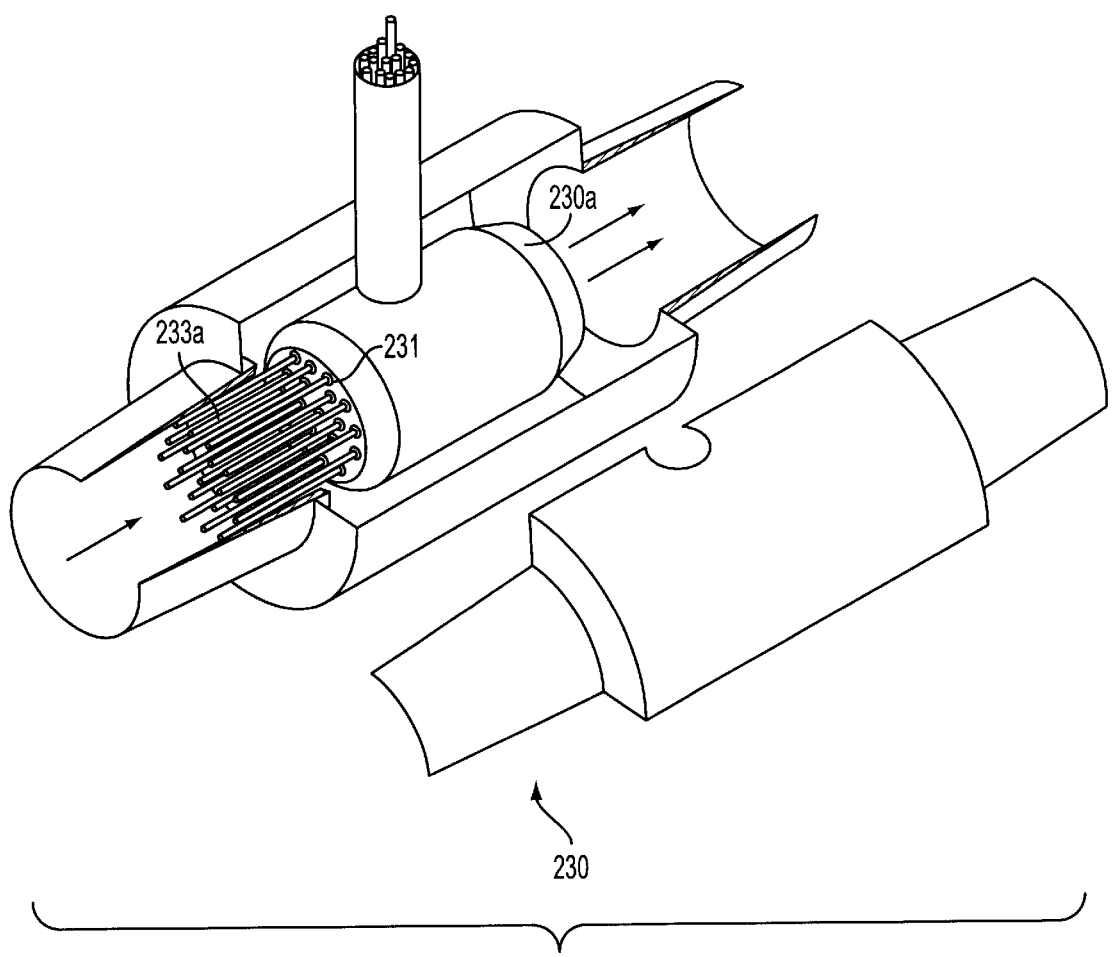
FIG. 5a illustrates the conductivity data collection apparatus for the data collection system.
Figure 5B:
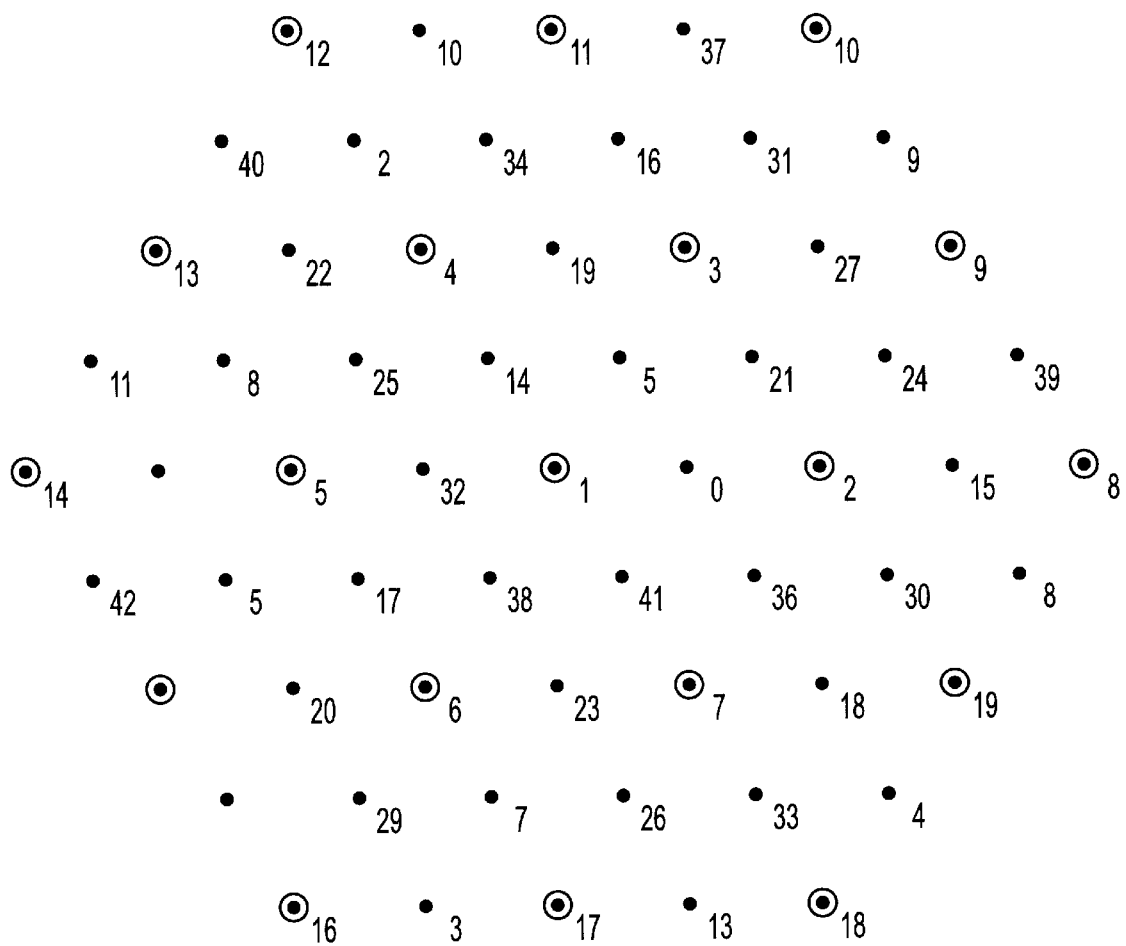
FIGS. 5b–5c illustrate additional details of a preferred embodiment of the conductivity data collection system.
Figure 5C:
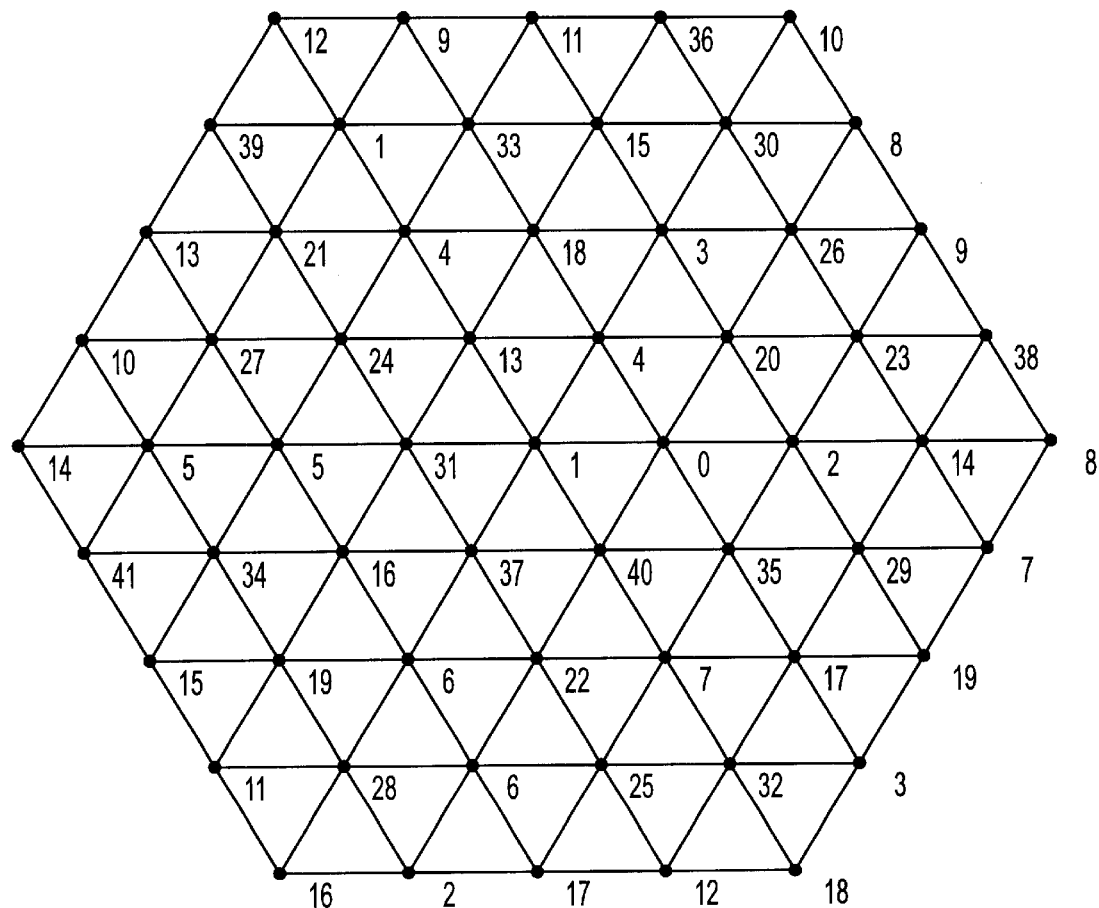

Also provided within the conduit 10 is a conductivity data collection subsystem 230 as shown in FIGS. 5a–5c including a conductivity probe 230a. The conductivity probe 230a comprises multiple regions of electrodes 233 to give a representation of the fluid being infused in each region of the conduit 10.

In a preferred embodiment, the conductivity probe 230a includes a sensor 231 having nineteen real electrodes 233a, mapped to forty-two regions 232. As shown in FIG. 5b, the conductivity probe 230a further includes forty-two primary virtual electrodes 233b, each of which are located at a midpoint between any two real electrodes 233a. Regions 232 are joined to provide sixty-two points. The sixty-two points connect to form ninety-six equilateral triangles, as shown in FIG. 5c. The addition of the virtual electrodes 233b increases the number of regions 232 thereby allowing finer measurements of concentration values. The data from the electrodes 233 is transmitted into a code processor (further described below) that in a preferred embodiment processes 800,000 triangles per second and 50 to 60 frames per second.

In the preferred embodiment, the conductivity probe 230a includes 19 Teflon insulated surgical stainless steel wires with uninsulated tips as real electrodes 233a. Other suitable metals may also be used for the wires forming the real electrode 233a cluster of sensor 231. The wires are preferably 0.19 mm in diameter, tapering slightly at the ends, and 25 mm in length. The Teflon coating is preferably 0.005 mm thick. Stainless steel fittings are used for the side of the real electrode 233a cluster of sensor 231. The stainless steel fittings are pressed in place, and the body of the conductivity probe 230a is counter-bored, so that there is no change in the inside diameter. A shielded cable connects the head of the conductivity probe 230a to additional data collection components.

C. Data Processing and Control System 300

Figure 3A:
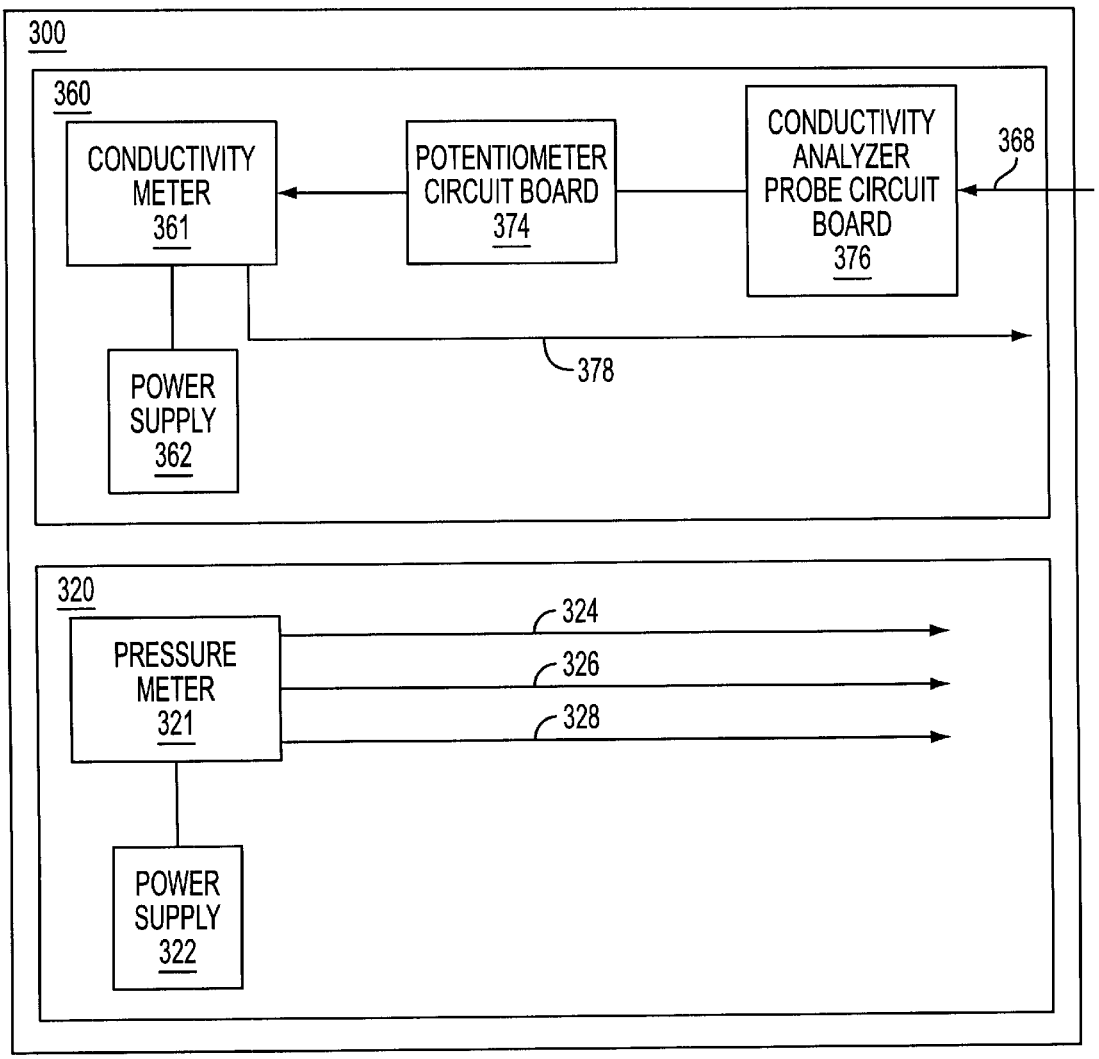
FIG. 3a is a block diagram showing the components of the data processing and control system.

The data collection system 200 sends all of the collected data to the data processing and control system 300 as shown in FIG. 3a. The data processing and control system 300 comprises two main subsystems. A first of these subsystems is a pressure monitoring subsystem 320 and a second subsystem is a conductivity monitoring subsystem 360.

1. Pressure Monitoring Subsystem 320

The operation of the infusion assembly 100 is controlled by the data processing and control system 300 as shown in FIG. 3. The data processing and control system 300 includes the pressure monitoring subsystem 320. The pressure monitoring subsystem 320 includes a pressure meter 321 powered by a power supply 322. A first output 324 of the pressure meter 321 sends a plurality of pressure signals to the user control and analysis system 500. A second output 326 of the pressure meter 321 sends a plurality of pressure signals to the infusion assembly 100, and a third output 328 of the pressure meter 321 sends a plurality of pressure signals to the display mechanism 400.

More specifically, the second output 326 delivers a plurality of electronic pressure signals to the infusion assembly 100 via a cable 329 to the stepper motor controller 148. A cable 318, which is preferably a rainbow ribbon cable, delivers a plurality of electronic pressure signals from the pressure monitoring subsystem 320 to a Commport 502 of the user control and analysis system 500.

Figure 3B:
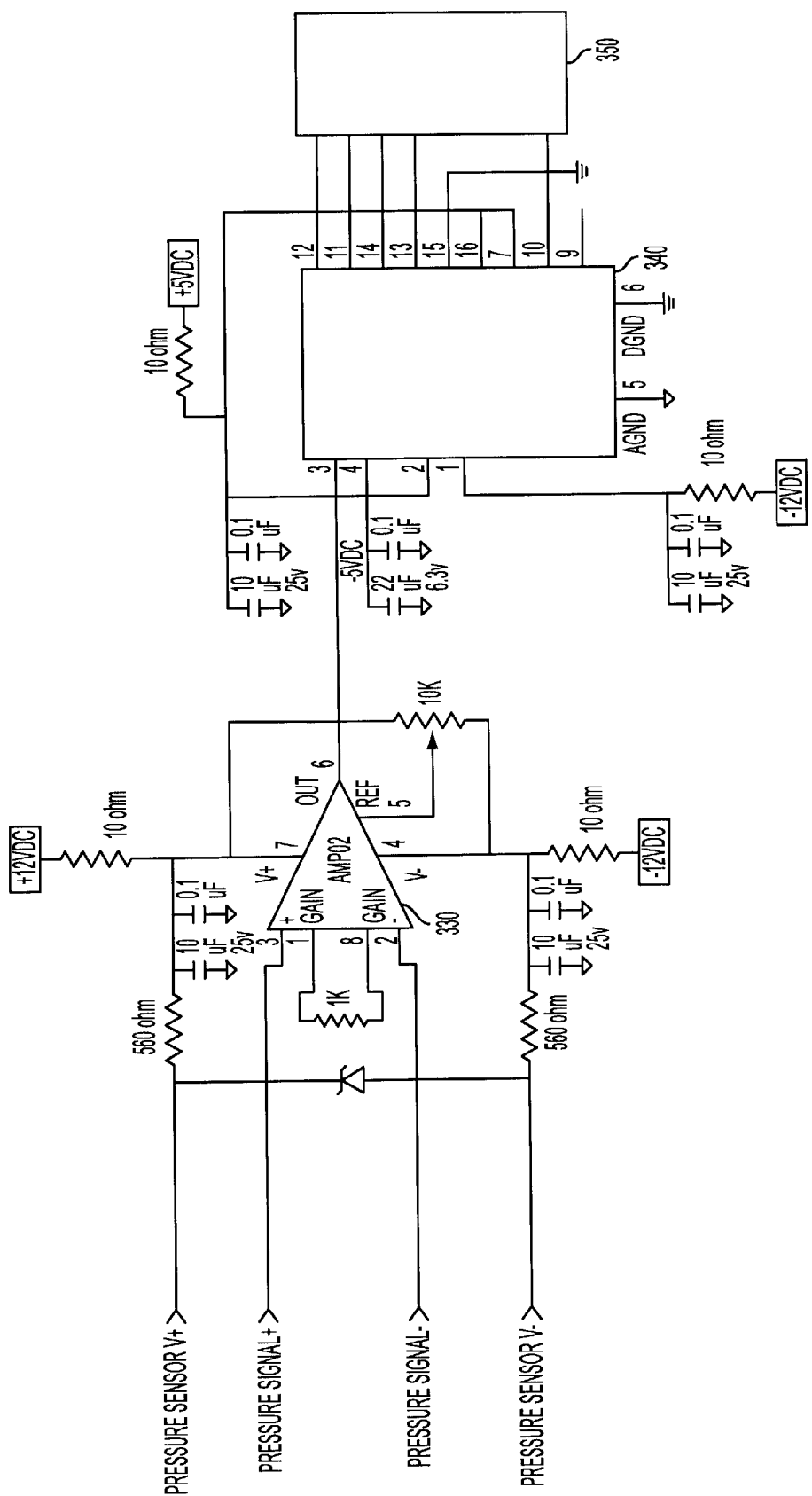
FIG. 3b illustrates the details of the pressure monitoring system.

As illustrated in FIG. 3b, the pressure meter 321 includes an amplifier 330, an A/D converter 340, and a CPU 350. Pressure signals from the pressure data collection subsystem 210 are forwarded to the amplifier 330 which outputs a plurality of signals to the A/D converter 340 and subsequently to the CPU 350 for output to other components of the system 1. FIG. 3b illustrates a preferred embodiment of the circuitry used for connecting the components of pressure meter 321, although specific resistance and capacitance values may be varied as appropriate.

It is through the above-described signal transmission that data provided from the pressure data collection subsystem 210 activates the pump 125. When the pressure of transducer 214 drops below a pre-selected level, the pump 125 starts. A constant pressure can thereby be created. The above-described solenoid valve 133 is programmed to open and close in accordance with the pulses received from the data processing and control system 300.

Pressure monitoring subsystem 320 uses several parameters to control pumping, including pulse width and dead time. In a preferred embodiment, pressure monitoring subsystem 320 is comprised of a microprocessor and an EPROM chip programmed to control the pressure using an assembly code programming language. The pressure monitoring subsystem 320 is thereby programmed to completely control pulse generation, operate the pump 125 at a constant pressure, and control the opening and closing of the solenoid valve 133. The pressure monitoring subsystem 320 is also programmed to limit the pulse width of the pulses generated to the solenoid valve 133 based on the pulses generated to the stepper motor 128. The pressure monitoring subsystem 320 is also programmed to monitor dead time, which determines the amount of time the solenoid valve 133 must stay off before another pulse. If the pressure exceeds a preselected threshold level, pumping will stop. Additionally, the pressure monitoring subsystem 320 may also be programmed to limit the total number of pulses that can be generated in one pumping session.

2. Conductivity Monitoring Subsystem 360

Also included in data processing and control system 300 is a conductivity monitoring subsystem 360 including a conductivity meter 361, powered by a power supply 362. An output 378 of the conductivity meter 361 is directed to the user control and data analysis system 500. An input 368 of the conductivity meter 361 is connected from the data collection system 200 to the conductivity meter 361 through a probe circuit board 376 and a potentiometer circuit board 374. The conductivity probe 230a within the data collection system 200 is mechanically mounted to the probe circuit board 376. Adjustment of a plurality of potentiometers on the potentiometer circuit board 374 provides a way of equalizing the total circuit resistance in each probe circuit.

Conductivity data processing and control begins with an input signal from the conductivity probe 230a to the probe circuit board 376. Through the input 368, a plurality of selector switches are provided and are used to activate a pair of the electrodes 233a in the electrode cluster of sensor 231 at any given point in time. The probe circuit board 376 repeatedly measures the conductivity difference between the electrodes 233a in the electrode cluster of sensor 231 by isolating one pair of electrodes 233a at a time. The conductivity between each activated, selected electrode pair 233a is measured by passing a small electrically-isolated constant voltage pulse from a voltage pulse source through the two activated, selected electrodes 233a. A voltage drop between the two activated, selected electrodes 233a is measured and is used to indicate a conductivity of the fluid in the conduit 10.

In a preferred embodiment, the probe circuit board 376 includes a pair of input multiplexer selector switches that are each sent a six bit sensor code which identifies the particular pair of electrodes 233a which is to be connected to a voltage pulse source. Each input multiplexer channel is normally an "open circuit," but any two input multiplexer channels can be activated simultaneously by sending the six bit sensor code to the channel to be connected to the voltage pulse source thus closing the channel and connecting an electrode 233a from the selected electrode 233a pair to the voltage pulse source causing to the other electrode 233a in the electrode pair to be connected to ground. The two electrode 233a sensor heads to be accessed are also connected to an instrumentation amplifier that measures the potential difference between the two accessed electrodes 233a. Independent multiplexers are also connected to the instrumentation amplifier so that an error is not introduced by a voltage drop in the current source/sink circuit. The time between accessing or activating any electrode 233a pair is less than one microsecond.

In the preferred embodiment, the input multiplexer is comprised of a 16 channel, dual 8-channel CMOS analog multiplexer, such as a DG406/DG407 multiplexer manufactured by Maxim Integrated Products. A conductivity meter 361 is comprised of a low voltage, low current pulse circuit—about 10 millivolts at 10 microamps—which provides the pulse to make the conductivity measurement. A voltage pulse is applied across a balanced circuit consisting of two resistors of equal resistivity value and a pair of electrodes 233a for which the conductivity measurement is to be made. The voltage between the pair of electrodes 233a will be dependent upon the conductivity of the fluid between them. The original voltage pulse is compared to the voltage pulse between the pair of electrodes 233a and the resulting difference is differentially amplified. This difference is captured by a peak detector and is then digitized by an A/D converter for processing by the user control and analysis system 500. Because the duration of the voltage pulse applied is extremely short, it effectively allows conductivity to be measured without probe capacitance or double layering.

Signals from the probe circuit board 376 are forwarded along the input 368 to the potentiometer circuit board 374 that includes a plurality of resistors to equalize electronic difference in the circuits of the different regions produced by the electrode 233 array.

Figure 3C:
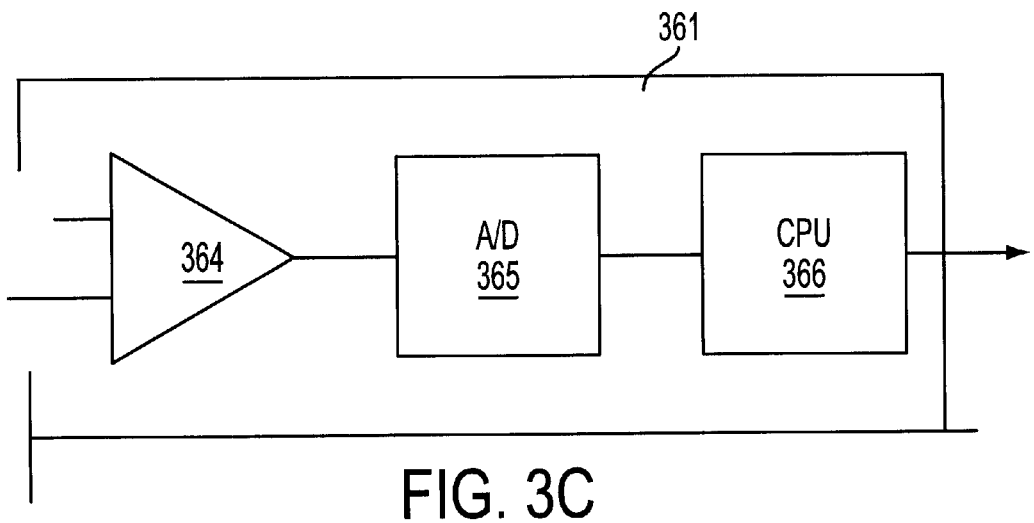
FIG. 3c illustrates additional components of the conductivity monitoring system.

From the potentiometer circuit board 374, signals are forwarded along the input 368 to the conductivity meter 361. The components of the conductivity meter 361 are shown in FIG. 3c. Signals are forwarded through an amplifier 364 and an A/D converter 365.

The amplifier 364 has three functions. First, it measures the voltage difference between an electrode 233 pair. Second, it amplifies the input voltage reading from an electrode 233 pair since the input voltage is lower than the dynamic range of the A/D converter 365 to which the amplifier 364 is connected. Finally, it buffers an output signal of the electrode 233 pair since the A/D converter 365 input draws several milliamps of current. In the preferred embodiment, the amplifier 364 is a 3-op amp design, such as the INA114 amplifier manufactured by Burr-Brown Corporation.

The A/D converter 365 receives the output from the amplifier 364 and converts the input analog voltage signal to a digital output signal to send to a control CPU 366. In the preferred embodiment, the A/D converter 365 is an A/D converter chip, such as one manufactured by Maxim Integrated Products. The A/D converter 365 preferably reads the input voltage every four microseconds giving a 250,000 sample second throughput.

The signal data are forwarded from A/D converter 365 to CPU 366. CPU 366 stores a region electrode 233 pair file that contains a list of six bit sensor codes for activating specific electrode 233 pairs. The CPU 366 outputs a six bit multiplexer control signal to the input multiplexer for selection of a specific electrode 233 pair. Additionally, CPU 366 receives a plurality of commands from the user control and analysis system 500.

A known problem in achieving accurate conductivity measurements relates to the passing of electric current through a saline solution. A phenomenon referred to as "double layering" occurs as the concentration goes up and the resistance goes down, thereby causing the solution to break down into ions.

Through testing, it was found that at 14 microseconds, before double layering occurs, pure current flows through the fluid without capacitance. Accordingly, accurate measurements can be taken during the initial time period of fluid flow, which in the system of the preferred embodiment, is approximately the first 14 microseconds.

An additional problem found in the original conductivity measurement scheme relates to the programming of A/D conversion. When the computer sees a "null," it begins taking readings of each of the 42 electrode regions 232. When the computer sees another "null" it begins taking readings again. However, sometimes, a natural zero occurs that the computer would interpret as a "null." This problem is solved by using the spare bits in a 16-bit memory word. The A/D value returned by the A/D converter 365 utilizes only 14 bits of the 16-bit word. One of the spare bits is always set to a valid A/D value while a "null" is sent as all "0" bits. The A/D converter 365 is preferably one manufactured by Maxim Integrated Products which utilizes a "2's" complement numbering system. The conductivity meter 361 converts the "2's" complement number to an unsigned positive binary value prior to sending information to the user control and analysis system 500.

D. Display Mechanism 400

The display mechanism 400 may include an oscilloscope 402 which is provided to show measured pressures. The oscilloscope 402 is preferably a 4-channel Hitachi oscilloscope. An additional oscilloscope 402 may be provided and is preferably a two-channel Hitachi oscilloscope. A motor pulse display 48 taps into the line from the pressure box to the stepper motor controller 148 for hookup to the oscilloscope 402. A ground terminal is provided for the stepper motor 148 pulse display on the oscilloscope 402.

E. User Control and Analysis System 500

Figure 6:
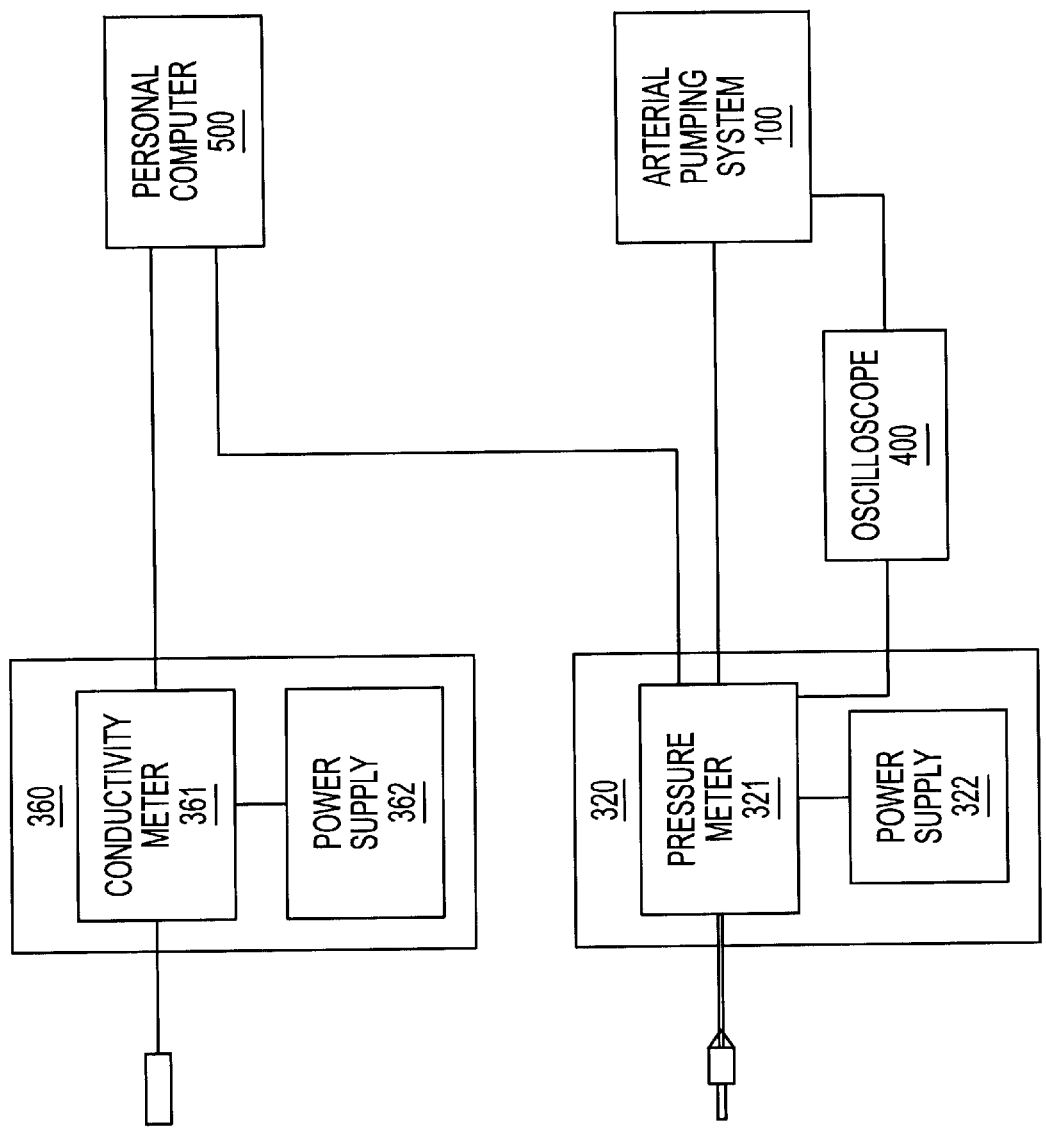
FIG. 6 is a block diagram showing a preferred embodiment of the components of the fluid monitoring and control system.

As shown in FIG. 6, the user control and analysis system 500 comprises a computer that is preferably a Gateway 2000 computer using a Windows®-based operating system. A main program running on a CPU 510 of the user control and analysis system 500 comprises multiple subprograms. The main program is interactive so that a user of system 1 can selectively view previously recorded analyses or portions thereof. The user can also select particular maps and graphs and change the format of these displays as desired. In operation, a user interface program is executed to allow a user to select items to be viewed. If the user selects a new electrode 233 pair, the program commands the user control and analysis system 500 to read in the region electrode 233 pair file. The six bit sensor codes control the input multiplexer selector switches to select a particular pair of electrodes 233.

As stated above, the main program running on the user control and analysis system 500 consists of several subprograms. After initialization, the main program will display several subprogram options for selection by the user. The various subprogram options are briefly described below.

An "about" subprogram is provided to create an "about box" for disclosing basic information about the main program.

A "calibrate" subprogram is provided to calibrate the probe 231. When selecting the "calibrate" subprogram, the user will be required to enter the concentration value of the known, second solution which is to be injected into the conduit 10 at the infusion sight. The probe 231 then takes a plurality of conductivity readings for each electrode 233 pair and these conductivity readings are recorded in a calibration table as calibration data points. If the probe 231 is replaced, a new calibration table must be created. A user can interact with the calibrate subprogram in order to delete or add calibration data points in the calibration table.

A "calpressure" subprogram allows for calculation of a plurality of pressure related values including an average pressure value, a maximum pressure value, a minimum pressure value, a diastolic pressure value, a systolic pressure value, and a pulse rate. The user can select one or more desired values and the calpressure subprogram will calculate the other values.

A "config" subprogram configures the display of electrode tables on the screen display of the user's computer including a real electrode 233a table, a virtual electrode 233b table, a triangle table and a hexagon table. The config subprogram ensures that proper distances between electrodes 233 will be displayed. The config subprogram allows the user to set various aspects of the configuration including the electrode delay time.

A "comm" subprogram facilitates the transfer of data from the data processing and control system 300 through a Commport 1 and a Commport 2 to the user control and analysis system 500. Specifically, the comm subprogram includes a read routine for reading bytes of data from the Commports 1 and 2 and sorts the data read into appropriate locations.

An "extensions" subprogram provides a definition for each of a plurality of macros that provide convenience to the user, such as a toolbar message macros, a progress bar extension macro, a track bar extension macro, and an up/down extension macro.

A "genmap" subprogram generates a plurality of maps that allow the real electrodes 233a and the virtual electrodes 233b to be plotted on the screen display of the user's computer. A graphical display subprogram also includes a region map image display function which identifies the parts of the screen which are reserved for each region 232 of the cross-section of the conduit 10. When displayed on the screen, each region 232 corresponds to a particular pair of sensor 231 electrodes 233 and will be displayed in a color that indicates a solution concentration of the particular pair of electrodes 233 currently under observation.

An "initialization" subprogram performs an initialization routine for each of the other subprograms in the main program. A plurality of windows and icons are created through this subprogram.

A "log" subprogram is provided to save data to a hard disk. The saved data may be transferred to a CD-ROM using a commercially available CD-ROM transfer program. The log subprogram further includes a sub-routine entitled "load observation." In this load observation sub-routine, a plurality of actual observations of solution concentration are stored to a disk for later display on the screen display of the user's computer. The log subprogram is interactive and allows the user to add comments to a log file.

A "mainframe" subprogram processes a plurality of messages for a main window and allows the user to select a plurality of appropriate context menus.

A "palette" subprogram creates a color palette to be used for display.

A "playback" subprogram allows the user to retrieve a stored client file and playback the recorded history of measured concentration and pressure values. This playback subprogram is capable of generating the display of a single frame for prolonged study or multiple frames in order to view an entire procedure or specified portion of a procedure. The playback subprogram can be implemented through the use of standard VCR components.

A "run" subprogram includes a routine for establishing a run time for the main program and for continuously displaying an elapsed time. The elapsed time is displayed in a run window that can be reconfigured at the request of the user.

A "screen" subprogram fills each triangular region 232 with specified colors corresponding to the concentration value of that region 232. The display image is updated constantly as the fluid flows through the conduit 10 and offers a real-time display of the solution concentration in the conduit 10.

A "setup" subprogram includes a plurality of routines that process a plurality of messages for the main window, setting a plurality of windows within the view of the user, canceling the windows, and determining an appropriate context to display.

A "triangle" subprogram defines a triangle class for an electrode configuration and a complete table structure to be displayed. The triangle subprogram includes a plurality of routines to construct and clear a hexagon table and a triangle table and to test for a new triangle. The triangle subprogram further includes a routine to generate a contour map implementing a plurality of colors of a palette.

The user control and analysis system 500 functions as an analysis system for both concentration and pressure data. The user control and analysis system 500 is able to give an accurate representation of the chemical agent which is being infused in each region 232.

Figure 7A:
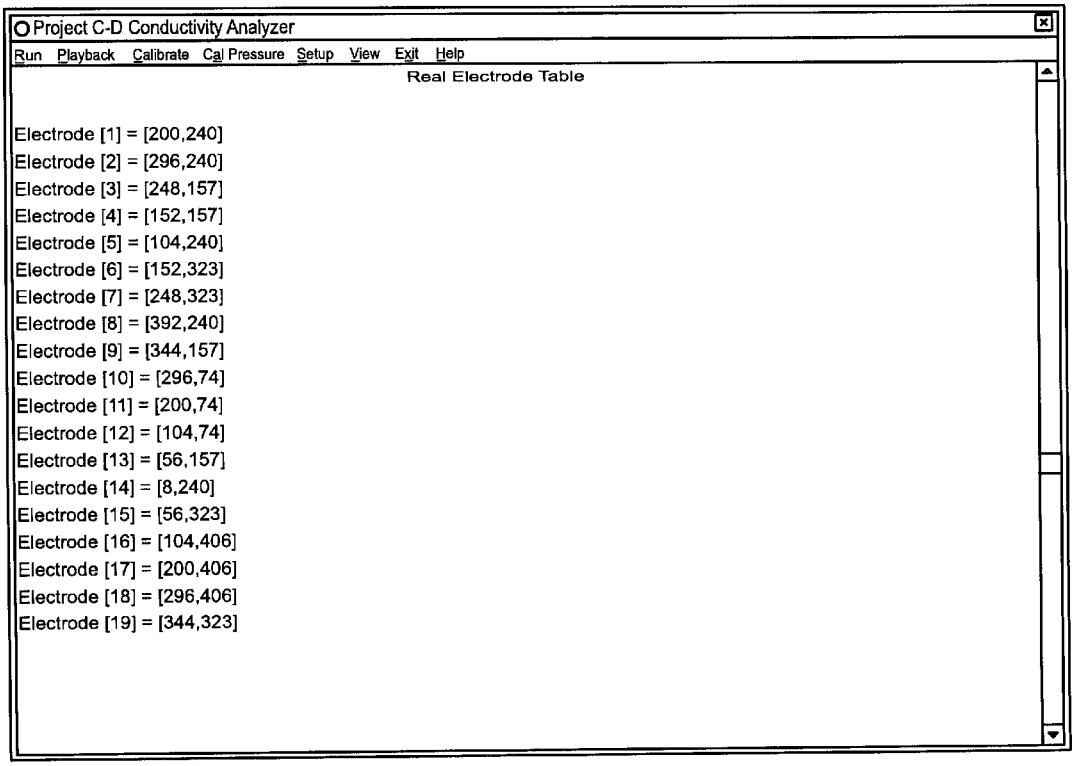
FIGS. 7a–7d are sample tables generated by the control and analysis system.
Figure 7A:
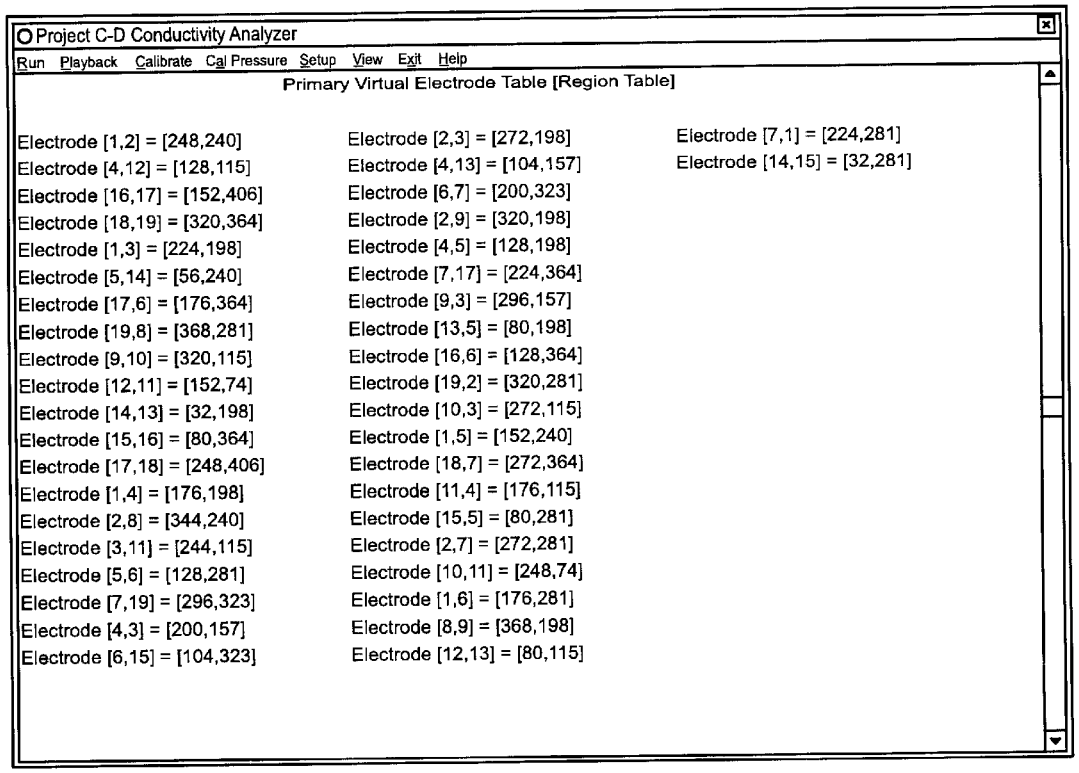
Figure 7B:
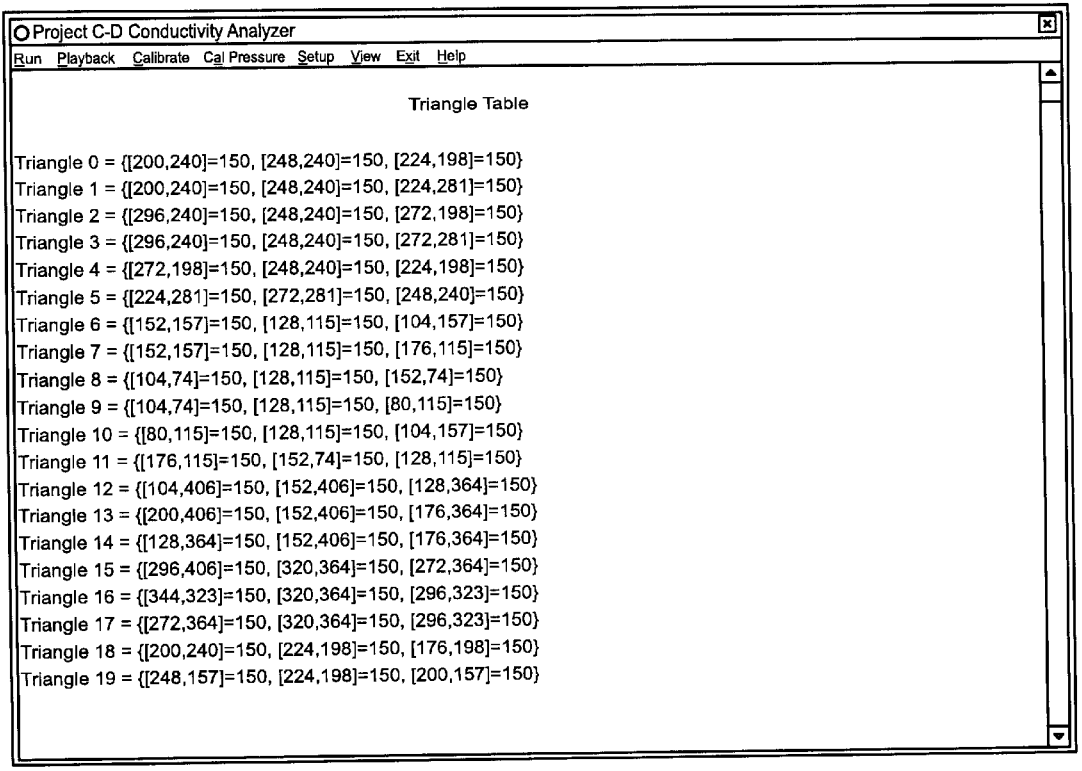
Figure 7B:
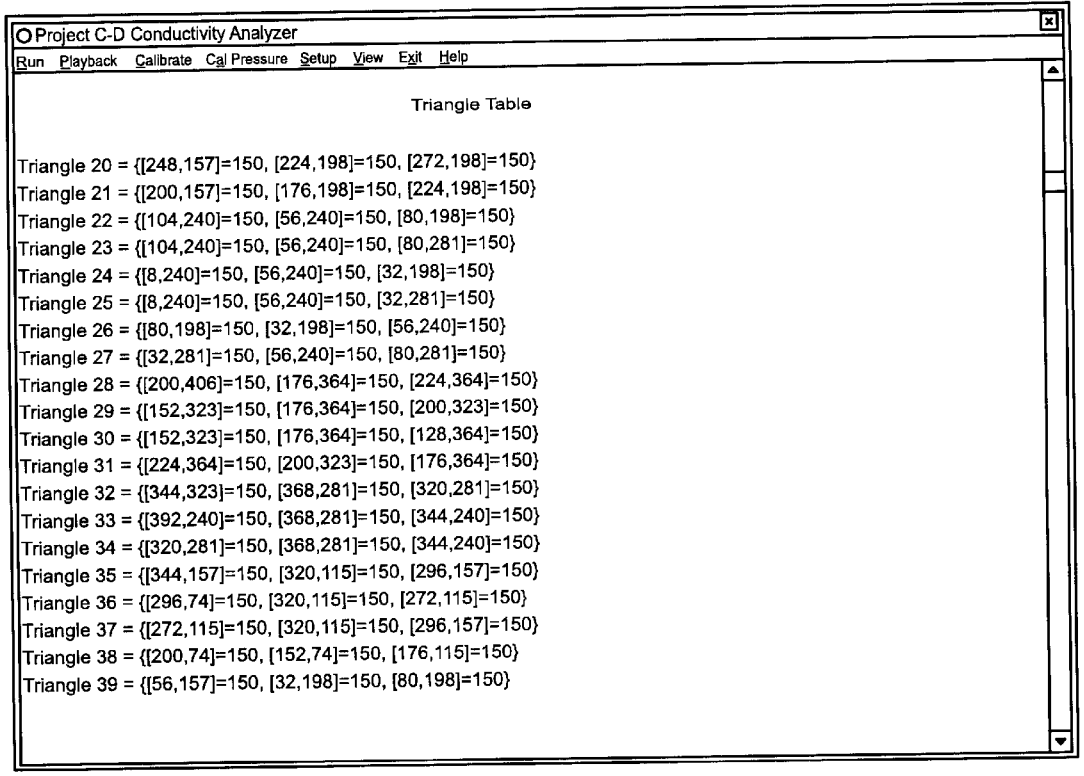
Figure 7C:
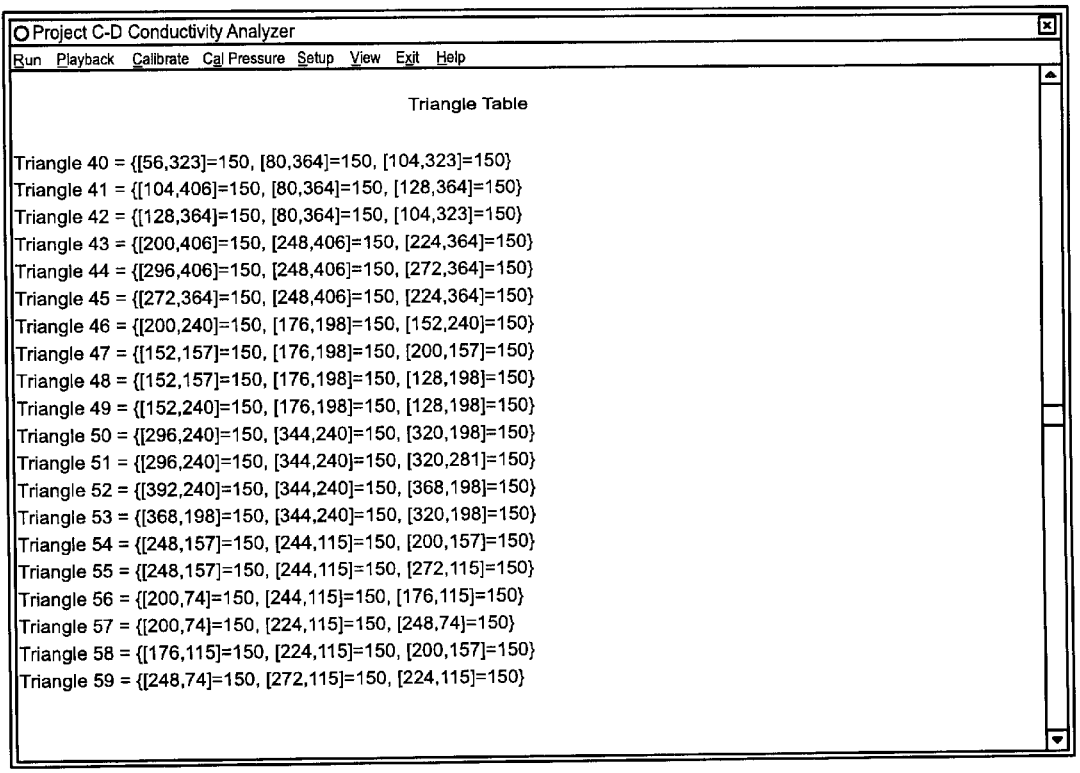
Figure 7C:
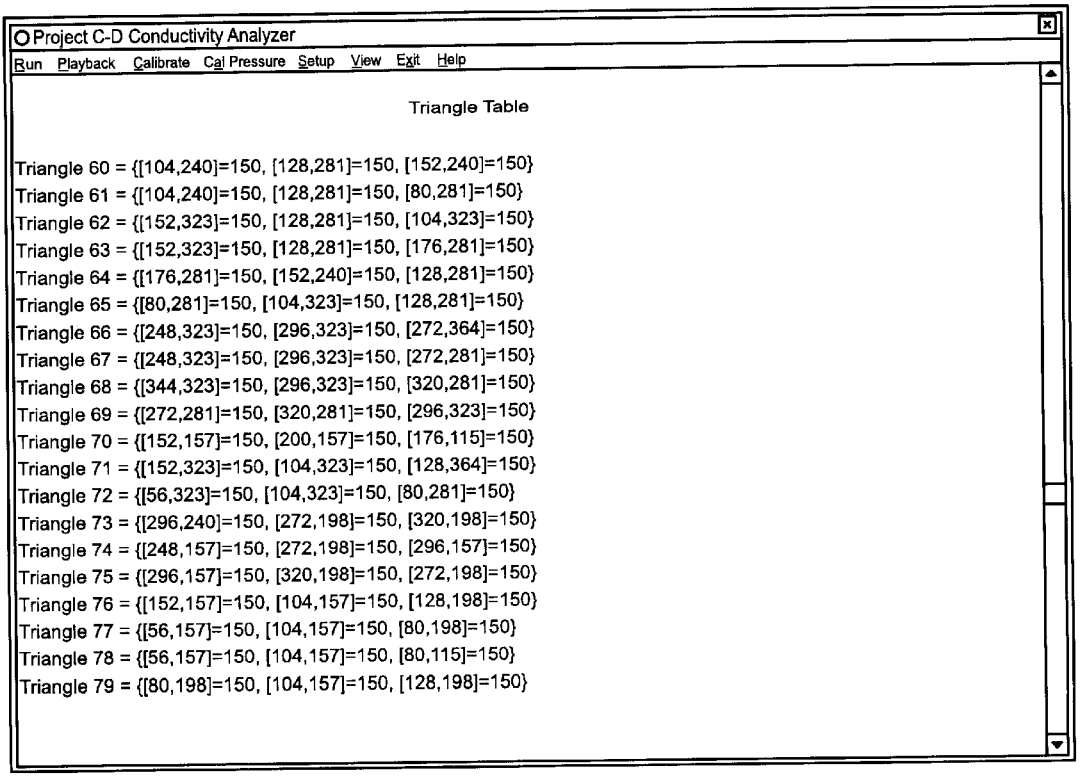
Figure 7D:
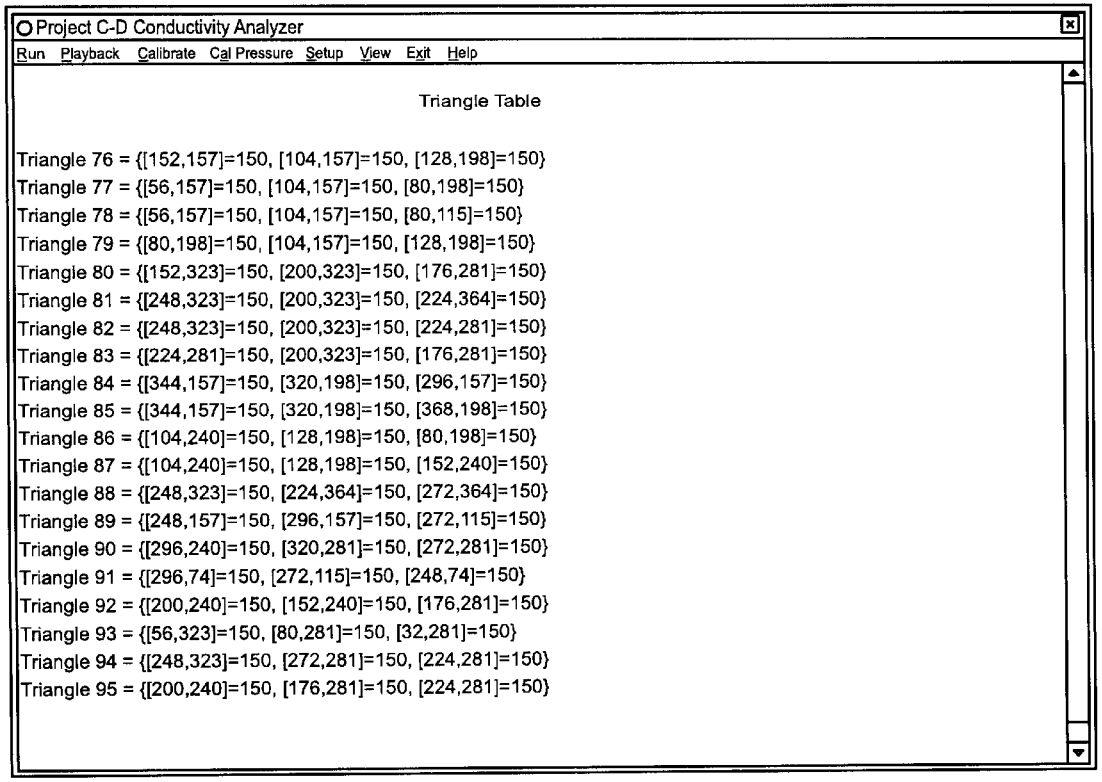

The user control and analysis system 500 allows the user to control, on a pulse-by-pulse basis, the distribution of fluid, the number of pulses, and all of the pressure parameters. A sample output of the user control and analysis system 500 is shown in FIGS. 7a–7d. FIG. 7a illustrates a real electrode 233a table and a virtual electrode 233b table. FIGS. 7b–7d illustrate sample triangle tables.

It will be apparent to those skilled in the art that various modifications and variations can be made in the system and method of the present invention without departing from the scope or spirit of the invention. Thus, it is intended that the present invention cover the modifications and variations of this invention provided as long as they come within the scope of the appended claims and their equivalents.

What is claimed is:

1. A system for monitoring and regulating pressure in a moving fluid stream inside of a conduit, the system comprising:
    an infusion assembly including,
        a catheter having a series of holes distributed around an exterior surface,
        injection means for introducing a fluid into the catheter, and
        a pump for delivering fluid to the injection means;
    a data collection system including,
        a first pressure transducer attached to a pressure chamber of the pump, and
        a second pressure transducer attached to an end of the catheter for measuring the pressure in a pressure chamber line of the catheter;
    a data processing and control system for processing data collected from the second pressure transducer attached to the end of the catheter and for controlling operations of the infusion assembly based on a comparison of a plurality of selected values and data received from the data collection system; and
    a user control and analysis system for allowing user interaction.

2. The system of claim 1, wherein the infusion assembly comprises a stepper motor and a stepper motor controller for powering the pump.

3. The system of claim 1, wherein the injection means comprises a syringe and wherein a solenoid valve controls pumping from the syringe to the catheter.

4. The system of claim 3, comprising a pumping electronic switch for providing a signal when the syringe is full and a refill electronic switch for providing a signal when the syringe is empty.

5. The system of claim 1, further comprising a pressure switch for setting a desired pumping pressure.

6. The system of claim 1, wherein the first pressure transducer is transducer in a wall of the conduit and the second pressure transducer is a piezo-resistive pressure transducer at a proximal end of the catheter.

7. The system of claim 1, wherein the data processing and control system comprises a pressure meter for outputting signals to the infusion assembly.

8. The system of claim 7, further comprising a pressure monitoring system including an amplifier, an A/D converter, and a CPU.

9. The system of claim 7, wherein the pressure meter comprises means for controlling infusion based on a plurality of pressure parameters including a pulse width and a dead time.

10. The system of claim 1, wherein the user control and analysis system allows the user to select one or more desired values and parameters.

11. A system for monitoring and regulating pressure and concentration in a moving fluid stream inside of a conduit, wherein the fluid stream includes a first fluid, the system comprising:
    an infusion assembly including,
        a catheter having a series of holes distributed around an exterior surface,
        injection means for introducing a second fluid into the catheter to create a solution mixture, and
        a pump for delivering the second fluid to the injection means;
    a data collection system including,
        a first pressure transducer attached to a pressure chamber of the pump,
        a second pressure transducer attached to an end of the catheter, and
        a sensor means within the conduit for measuring a conductivity of the solution mixture;
    data processing and control apparatus including conversion means for converting the measured conductivity into a concentration value, and control means for controlling operation of the infusion assembly based on a comparison of a plurality of selected values with data received from the data collection system; and
    a user control and analysis system for allowing user interaction.

12. The system of claim 11, wherein the sensor means within the conduit comprises a probe having a plurality of real electrodes.

13. The system of claim 12, wherein the probe comprises nineteen real electrodes.

14. The system of claim 12, wherein a primary virtual electrode is disposed at a midpoint between any two of the real electrodes.

15. The system of claim 14, wherein the real electrodes and the primary virtual electrodes are capable of being connected to form ninety-six equilateral triangles for analysis of conductivity in a plurality of specified regions inside of the conduit.

16. The system of claim 11, wherein the data processing and control system calculates conductivity in a specified region of the conduit by calculating the conductivity in a region between two electrodes.

17. The system of claim 11, further comprising means for prompting conductivity measurements during an initial period of flow of the second fluid through the catheter, the initial period being between 10 and 18 $\mu s$.

18. The system of claim 11, wherein the data processing and control apparatus comprises a conductivity meter including an amplifier, an A/D converter, and a CPU for processing conductivity measurements taken by the data collection system.

19. The system of claim 18, wherein the A/D converter comprises a microprocessor chip programmed using a hexadecimal assembly programming language.

20. The system of claim 11, wherein the user control and analysis system comprises one or more pull down menus for the user to select one or more viewing options.

21. The system of claim 11, wherein the user control and analysis system allows the user to select one or more of a plurality of specific measurement regions by selecting one or more electrode pairs.

22. The system of claim 11, wherein the control means allows a user to select a pressure threshold.

23. The system of claim 11, wherein the control means allows the user to select to replay a pre-recorded test data.

24. The system of claim 11, wherein the infusion assembly comprises a stepper motor and a stepper motor controller for powering the pump.

25. The system of claim 11, wherein the injection means comprises a syringe and wherein a solenoid valve controls pumping from the syringe to the catheter.

26. The system of claim 25, further comprising a pumping electronic switch for providing a signal when the syringe is full and a refill electronic switch for providing a signal when the syringe is empty.

27. The system of claim 11, further comprising a pressure switch for setting a desired pumping pressure.

28. The system of claim 11, wherein the first pressure transducer is transducer in a wall of the conduit and the second pressure transducer is a piezo-resistive pressure transducer at a proximal end of the catheter.

29. The system of claim 11, wherein the data processing and control system comprises a pressure meter for outputting signals to the infusion assembly.

30. The system of claim 29, further comprising a pressure monitoring system that includes an amplifier, an A/D converter, and a CPU.

31. The system of claim 29, wherein the pressure meter comprises means for controlling infusion based on a plurality of pressure parameters including a pulse width and a dead time.

* * * * *